(12) United States Patent
Shimada et al.

(10) Patent No.: US 7,134,317 B2
(45) Date of Patent: Nov. 14, 2006

(54) METHOD OF DETECTING A HYDROGEN CONCENTRATION AND APPARATUS FOR DETECTING HYDROGEN

(75) Inventors: Toshiaki Shimada, Wako (JP); Yoshio Nuiya, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 216 days.

(21) Appl. No.: 10/942,514

(22) Filed: Sep. 16, 2004

(65) Prior Publication Data
US 2005/0066706 A1 Mar. 31, 2005

(30) Foreign Application Priority Data
Sep. 30, 2003 (JP) ............... 2003-340170

(51) Int. Cl.
G01N 29/02 (2006.01)
G01N 7/00 (2006.01)

(52) U.S. Cl. .............. 73/23.2; 73/23.31; 73/31.05
(58) Field of Classification Search ............ 73/23.2, 73/23.31, 31.05
See application file for complete search history.

(56) References Cited

U.S. PATENT DOCUMENTS 6,155,099 A * 12/2000 Kobayashi et al. ........ 73/31.05
6,596,236 B1 * 7/2003 DiMeo et al. ............ 422/88

FOREIGN PATENT DOCUMENTS

| JP | 1-307636 | * | 12/1989 | .............. 73/31.05 |
| JP | 2-259458 | * | 10/1990 | .............. 73/31.05 |
| JP | A-10-73530 | | 3/1998 | |
| JP | 2004-37146 | * | 2/2004 | .............. 73/31.05 |

* cited by examiner

Primary Examiner—Daniel S. Larkin
(74) Attorney, Agent, or Firm—Hamre, Schumann, Mueller & Larson, P.C.

(57) ABSTRACT

In a hydrogen concentration detecting method of detecting whether the hydrogen concentration is equal to or higher than a reference concentration; using a hydrogen detecting apparatus 1 comprising a detecting element 4 made of a hydrogen absorbing alloy, a microheater 2, a substrate 3, and a strain gauge 6, where the operation of the microheater 2 is halted during a normal state; however, once the strain gauge 6 detects a volume change of the detecting element 4, the microheater 2 starts heating the detecting element 4.

4 Claims, 3 Drawing Sheets

METHOD OF DETECTING A HYDROGEN CONCENTRATION AND APPARATUS FOR DETECTING HYDROGEN

This application claims foreign priority based on Japanese Patent application No. 2003-340170, filed Sep. 30, 2003, the contents of which is incorporated herein by reference in its entirety.

BACKGROUND OF THE INVENTION

1. Field of the Invention

The present invention relates to a whether a hydrogen concentration in a gas is equal to or higher than a reference concentration, and also to an apparatus for detecting hydrogen.

2. Description of the Related Art

An apparatus for detecting hydrogen using a hydrogen absorbing alloy is disclosed in JP-A-10-73530. In the hydrogen detecting apparatus, a hydrogen absorbing alloy is fixed to one of the sides of a substrate, while a strain gauge is attached to another side thereof. In this structure, the stain gauge detects strain of the substrate caused by volume expansion of the hydrogen absorbing alloy in case of absorbing hydrogen. Concerning the hydrogen detecting apparatus using a hydrogen absorbing alloy, its selectivity with respect to hydrogen may be rather high, whereby the hydrogen detecting apparatus has an advantage in its high detection accuracy.

It is known that such a hydrogen absorbing alloy has P-T characteristics, where the hydrogen absorbing pressure might be uniquely determined in accordance with the operation temperature. Therefore, in a related art, a hydrogen detecting apparatus having the following manner has been developed. That is, an output of the strain gauge is monitored in a state where the operation temperature is always kept constant using a heater and the like. When a change occurs in the output of the stain gauge under said condition, the concentration of hydrogen is determined in that the detected gas reaches the concentration which corresponds to the hydrogen absorbing pressure according to the operation temperature as disclosed in JP-A-10-73530.

However, there is a drawback in such a hydrogen detecting apparatus, because keeping the condition of the constant temperature for the operation requires the continuous temperature control, and hence the heater must be energized for a long time period. In this regard, in case of the hydrogen concentration being monitored for a long term, the power consumption of the heater becomes very large, which ends up being costly. Moreover, the power supply source might be configured in relatively large size, which ends up increasing the manufacturing cost.

Especially, in the case of a hydrogen detecting apparatus which is disposed in a mobile unit, such as a fuel cell vehicle, which must be operated by the power supplied by a battery of which capacity is inevitably limited, and therefore, there is always the request to reduce power consumption. In this regard, it is disadvantageous for a fuel cell vehicle to increase the size of the battery.

SUMMARY OF THE INVENTION

It is an object of the invention to provide a method of detecting a hydrogen concentration and an apparatus for detecting hydrogen in which energy required for detecting a hydrogen concentration can be reduced.

In order to attain the object, the invention provides a hydrogen concentration detecting method of detecting whether a hydrogen concentration is equal to or higher than a reference concentration, using a hydrogen detecting apparatus (for example, a hydrogen detecting apparatus 1 in an embodiment described later) including a detecting element made of a hydrogen absorbing alloy which absorbs hydrogen of a reference concentration at a reference temperature that is higher than an atmospheric temperature (for example, a detecting element 4 in the embodiment described later); heating means for heating a detecting element (for example, a microheater 2 and a substrate 3 in the embodiment described later); and change detecting means for detecting a change of a physical property value when the detecting element absorbs hydrogen (for example, a strain gauge 6 in the embodiment described later), wherein The method comprises:

monitoring said change detecting means for a change of the physical property value of said detecting element with said heating means operationally off; and when said change detecting means detects a change of the physical property value of said detecting element, turning an operationally said heating means to heat said detecting element.

According to the hydrogen concentration detecting method of the first aspect in this invention, in a normal state, the operation of the heating means is halted so as not to heat the detecting element, and hence the temperature of the detecting element substantially coincides with the atmospheric temperature. When the hydrogen partial pressure of the atmosphere is lower than the hydrogen equilibrium pressure according to the atmospheric temperature, the detecting element does not absorb hydrogen, and, when the hydrogen partial pressure of the atmosphere is higher than the hydrogen equilibrium pressure according to the atmospheric temperature, the detecting element absorbs hydrogen.

In the case where the reference temperature is set to be higher than the atmospheric temperature in a normal state, when the hydrogen concentration of the atmosphere is equal to or higher than the reference concentration, the detecting element always absorbs hydrogen at normal temperature, and, when the hydrogen concentration of the atmosphere is lower than the reference concentration, the detecting element absorbs hydrogen at normal temperature or does not absorb hydrogen depending on the hydrogen concentration of the atmosphere and the atmospheric temperature.

Only when it is determined during stoppage of the operation of the heating means that the detecting element absorbs hydrogen, the heating means is operated to start the operation of heating the detecting element. According to the configuration, it is not required to always operate the heating means, and, during a period when it is determined during stoppage of the operation of the heating means that the detecting element does not absorb hydrogen, the operation of the heating means can be kept halted. Therefore, the energy required for detecting the hydrogen concentration can be reduced.

Further, the hydrogen concentration detecting method of the second aspect in this invention may be configured so that, in the hydrogen concentration detecting method of the first aspect, after the heating means is operated, when the detecting element stops absorption of hydrogen before a temperature of the detecting element reaches the reference temperature, the operation of the heating means is halted.

When, after the operation of heating the detecting element is started, the detecting element stops absorption of hydrogen before the temperature reaches the reference temperature, and it is possible to determine that the hydrogen concentration of the atmosphere is lower than the reference concentration. Therefore, the operation of the heating means is halted, and unnecessary operation of the heating means can be eliminated.

According to the third aspect in this invention, an apparatus for detecting hydrogen in this invention comprises: a detecting element made of a hydrogen absorbing alloy which absorbs hydrogen of a reference concentration at a reference temperature that is higher than an atmospheric temperature (for example, the detecting element 4 in the embodiment described later); heating means for heating the detecting element (for example, the microheater 2 and the substrate 3 in the embodiment described later); change detecting means for detecting a change of a physical property value when the detecting element absorbs hydrogen (for example, the strain gauge 6 in the embodiment described later); hydrogen absorption determining means for, determining whether the change detecting means detects a change of the physical property value or not (for example, step S102 in the embodiment described later) during a state of an operation of the heating means being halted; and heating conducting means for, if the hydrogen absorption determining means determines that a change of the physical property value is detected, conducting the heating means to operate (for example, step S103 in the embodiment described later).

According to the configuration, in a normal state, the operation of the heating means is halted, and, when the detecting means detects a change of the physical property value of the detecting element during stoppage of the operation of the heating means, the heating means is operated to heat the detecting element, so that the hydrogen concentration of the atmosphere can be detected.

According to fourth aspect of this invention, the hydrogen detecting apparatus may be configured so that, in the hydrogen detecting apparatus of the third aspect, the apparatus further comprises: temperature detecting means for detecting a temperature of the detecting element (for example, a temperature sensor 5 in the embodiment described later); and heating halting means for halting the operation of the heating means (for example, step S107 in the embodiment described later) when the detecting element stops absorption of hydrogen before a temperature of the detecting element reaches the reference temperature while the heating means is operated.

According to the configuration, when, after the operation of the heating means is started, the detecting element stops absorption of hydrogen before the temperature reaches the reference temperature, it is possible to stop the operation of the heating means.

According to the invention of the first aspect, it is not required to always operate the heating means, and, during a period when it is determined during stoppage of the operation of the heating means that the detecting element does not absorb hydrogen, the operation of the heating means can be kept halted. Therefore, the energy required for detecting the hydrogen concentration can be reduced. As a result, the size of the energy supply source can be reduced, and the running cost can be lowered.

According to the invention of the second aspect, unnecessary operation of the heating means can be eliminated. Therefore, it is possible to prevent the heating means from wastefully consuming energy.

According to the invention of the third aspect, in a normal state, the operation of the heating means is halted, and, when the detecting means detects a change of the physical property value of the detecting element during stoppage of the operation of the heating means, the heating means is operated to heat the detecting element, so that the hydrogen concentration of the atmosphere can be detected. Consequently, it is not required to always operate the heating means, and, during a period when it is determined during stoppage of the operation of the heating means that the detecting element does not absorb hydrogen, the operation of the heating means can be kept halted. Therefore, the energy required for detecting the hydrogen concentration can be reduced. As a result, the size of the energy supply source can be reduced, and the running cost can be lowered.

According to the invention of fourth aspect, when, after the operation of the heating means is started, the detecting element stops absorption of hydrogen before the temperature reaches the reference temperature, and it is possible to stop the operation of the heating means. Therefore, unnecessary operation of the heating means can be eliminated, and it is possible to prevent the heating means from wastefully consuming energy.

DESCRIPTION OF THE PREFERRED EMBODIMENTS

Figure 1:
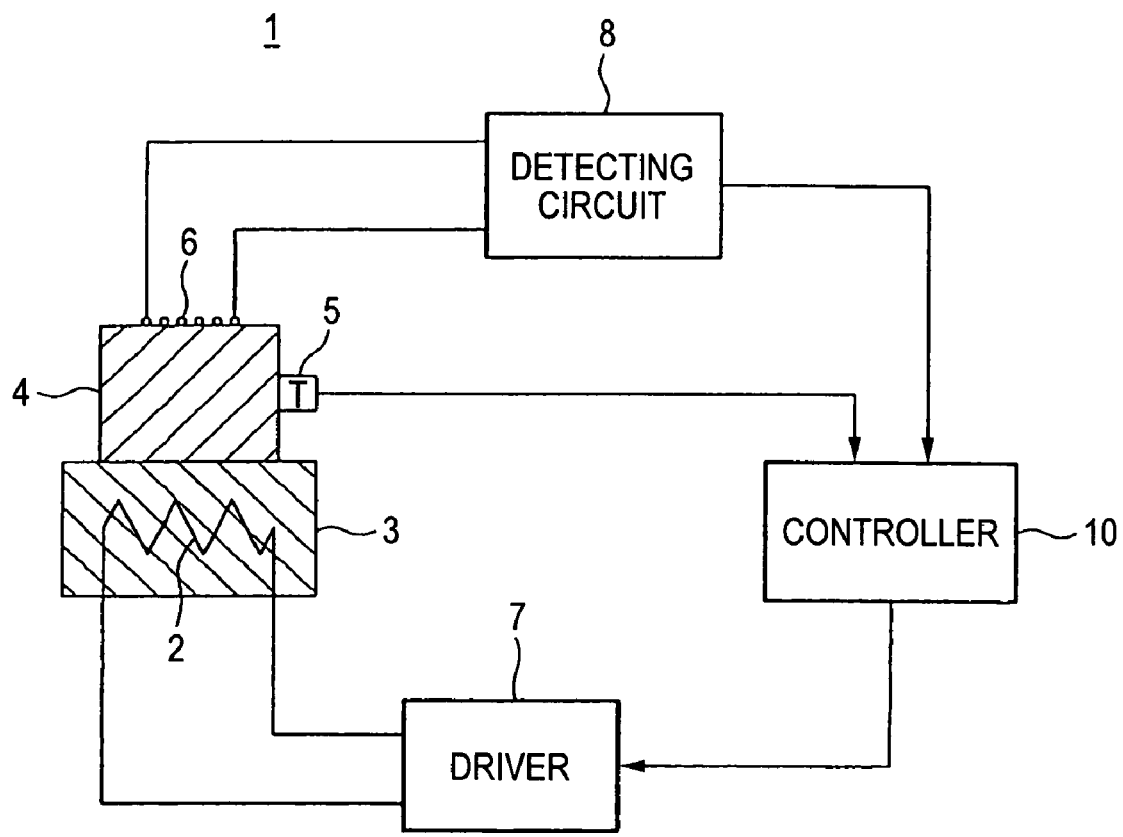
FIG. 1 is a section view of an embodiment of the hydrogen detecting apparatus of the invention.

Hereinafter, an embodiment of the hydrogen concentration detecting method and the hydrogen detecting apparatus of the invention will be described with reference to FIGS. 1 to 4.

First, the configuration of a hydrogen detecting apparatus 1 will be described with reference to FIGS. 1 and 2. The hydrogen detecting apparatus 1 comprises: a substrate 3 in which a microheater 2 is embedded; a detecting element 4 which is attached to the upper face of the substrate 3; a temperature sensor (temperature detecting means) 5 which detects the temperature of the detecting element 4; and a strain gauge (change detecting means) 6 which is attached to the upper face of the detecting element 4.

The substrate 3 functions as a base for supporting the detecting element 4, and also as a heating plate for heating the detecting element 4. The microheater 2 is placed so as to uniformly heat substantially the whole substrate 3, and the ON/OFF control states can be performed by a controller 10 via a driver 7. In the embodiment, the microheater 2 and the substrate 3 constitute the heating means.

The detecting element 4 is made of a hydrogen absorbing alloy, and bonded firmly and closely to the substrate 3 by adequate means having excellent heat resistance, such as sintering, pressure bonding, thermal spraying, or adhesion. For example, the bonding is conducted by applying a slurry-like hydrogen absorbing alloy to the substrate 3.

Figure 3:
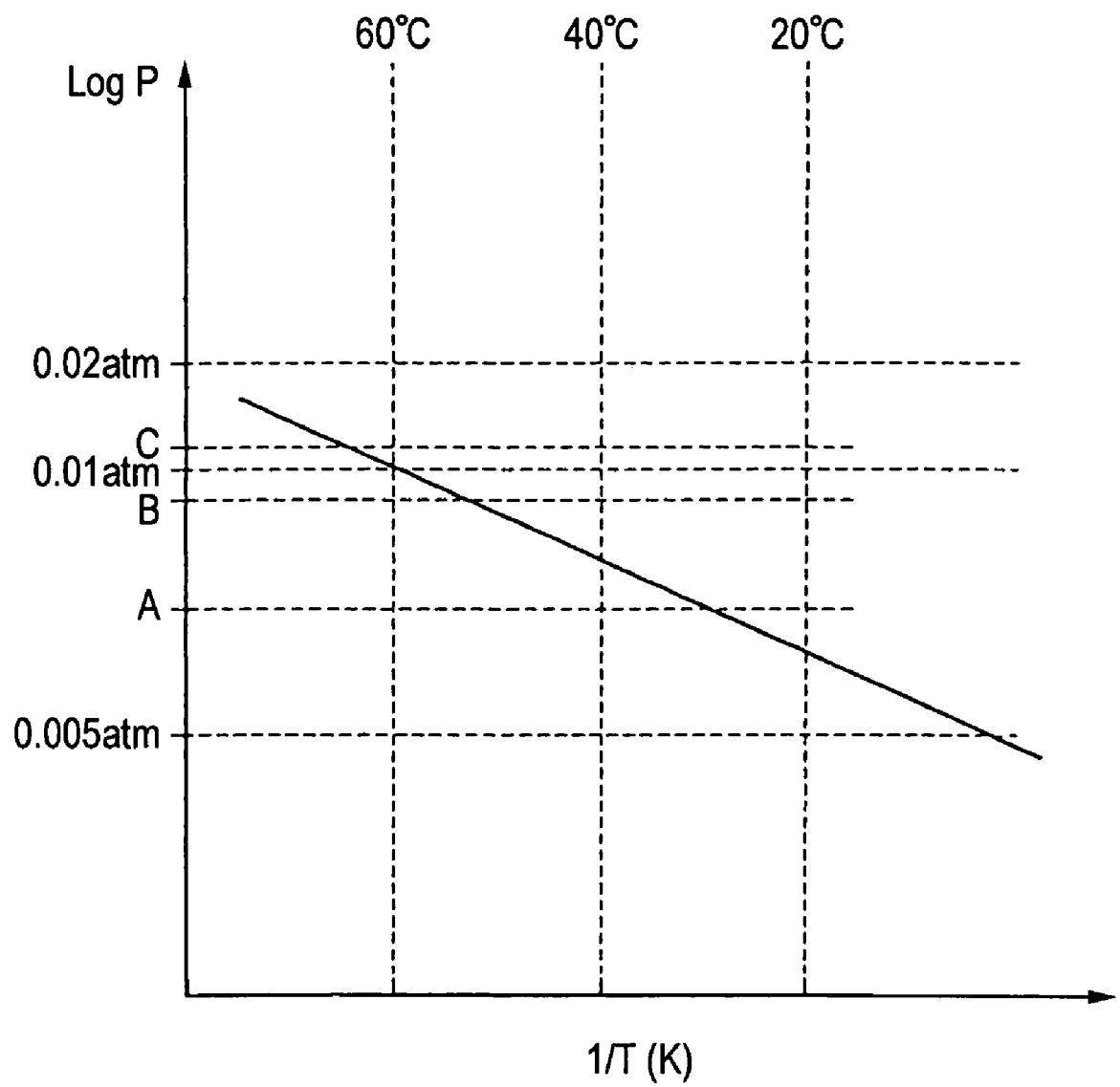
FIG. 3 is a view showing the P-T characteristics of a hydrogen absorbing alloy used in the hydrogen detecting apparatus of the embodiment.

FIG. 3 shows the P-T characteristics of the hydrogen absorbing alloy used in the detecting element 4 of the embodiment. In the figure, the ordinate shows the logarithm of the hydrogen absorbing pressure (log P), and the abscissa shows the reciprocal of the absolute temperature of the hydrogen absorbing alloy (1/T). In the P-T characteristics of the hydrogen absorbing alloy, the hydrogen equilibrium pressure is higher as the temperature of the hydrogen absorbing alloy is higher. The hydrogen equilibrium pressure is a generic term for the hydrogen absorbing pressure and the hydrogen desorbing pressure in the case where a hysteresis is not problematic.

In the embodiment, the reference temperature of the hydrogen detecting apparatus 1 is set to 60° C., and the hydrogen equilibrium pressure of the hydrogen absorbing alloy at the reference temperature of 60° C. is 0.01 atm. In the corresponding relationships between the hydrogen partial pressure in the atmospheric air and the hydrogen concentration, a hydrogen partial pressure of 0.01 atm corresponds to the hydrogen concentration of 1.0%.

The hydrogen absorbing alloy has characteristics in which, when the alloy absorbs hydrogen, the volume expands, the alloy generates heat, and the weight is increased.

Figure 2:
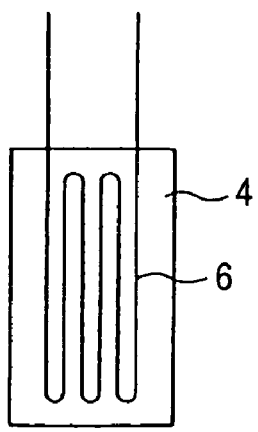
FIG. 2 is a plan view of a detecting element in the hydrogen detecting apparatus of the embodiment.

As shown in FIGS. 1 and 2, the strain gauge 6 is bonded integrally to the upper face of the detecting element 4 by a heat-resistant adhesive agent or the like. The strain gauge 6 itself also has heat resistance. The strain gauge 6 detects strain which is produced in the strain gauge 6 when the hydrogen absorbing alloy constituting the detecting element 4 absorbs hydrogen and the volume of the alloy expands, as a change in electrical resistance. The change in electrical resistance is detected by a detecting circuit 8, and the detection signal is supplied to the controller 10.

Also, an output signal of the temperature sensor 5 is supplied to the controller 10.

Next, the hydrogen concentration detecting method using the hydrogen detecting apparatus 1 will be described.

When the hydrogen partial pressure of the atmosphere where the hydrogen detecting apparatus 1 is disposed is lower than the hydrogen equilibrium pressure according to the temperature, the hydrogen absorbing alloy constituting the detecting element 4 discharges hydrogen, and, when the hydrogen partial pressure is equal to or higher than the hydrogen equilibrium pressure according to the temperature, the hydrogen absorbing alloy absorbs hydrogen. When the hydrogen absorbing alloy absorbs hydrogen, the volume of the alloy expands, and hence a change of the electric resistance of the strain gauge 6 attached to the detecting element 4 is detected by the detecting circuit 8. When strain is detected by the strain gauge 6, therefore, it is determined that the detecting element 4 absorbs hydrogen, and, when strain is not detected by the strain gauge 6, it is determined that the detecting element 4 does not absorb hydrogen.

In the embodiment, the temperature of the atmosphere where the hydrogen detecting apparatus 1 is disposed is about 20° C. in a normal state, and about 40° C. at the maximum. The hydrogen detecting apparatus 1 is used for giving an alarm when the hydrogen concentration of the atmosphere where the hydrogen detecting apparatus 1 is disposed is 1% or higher.

In the hydrogen detecting apparatus 1, in a normal state, the microheater 2 is turned OFF so that the detecting element 4 is not heated. In this state, therefore, the temperature of the detecting element 4 substantially coincides with the atmospheric temperature. When the hydrogen partial pressure of the atmosphere is lower than the hydrogen equilibrium pressure according to the atmospheric temperature, the detecting element 4 does not absorb hydrogen, and, when the hydrogen partial pressure of the atmosphere is equal to or higher than the hydrogen equilibrium pressure according to the atmospheric temperature, the detecting element 4 absorbs hydrogen. As described above, the atmospheric temperature in a normal state is 40° C. at the maximum, and lower than the reference temperature of 60° C. In a normal state, therefore, the hydrogen equilibrium pressure of the hydrogen absorbing alloy constituting the detecting element 4 is lower than that at the reference temperature. When the hydrogen concentration of the atmosphere is equal to or higher than 1%, consequently, the detecting element 4 always absorbs hydrogen at normal temperature. By contrast, when the hydrogen concentration of the atmosphere is lower than 1%, the detecting element 4 absorbs hydrogen in a normal state or does not absorb hydrogen depending on the hydrogen concentration of the atmosphere and the atmospheric temperature.

For example, the case where the hydrogen concentration of the atmosphere is A in FIG. 3 will be considered. When the atmospheric temperature is 20° C., the detecting element 4 absorbs hydrogen, but, when the atmospheric temperature is 40° C. or 60° C., the detecting element does not absorb hydrogen. In the case where the hydrogen concentration of the atmosphere is B in FIG. 3, when the atmospheric temperature is 20° C. or 40° C., the detecting element 4 absorbs hydrogen, but, when the atmospheric temperature is 60° C., the detecting element does not absorb hydrogen. In the case where the hydrogen concentration of the atmosphere is C in FIG. 3, when the atmospheric temperature is at any one of 20° C., 40° C., and 60° C., the detecting element 4 absorbs hydrogen.

In the hydrogen concentration detecting method of the embodiment, only when it is determined that the detecting element 4 absorbs hydrogen in the normal state where the microheater 2 is turned OFF and the operation of heating the detecting element 4 is not conducted, the microheater 2 is turned ON to start an operation of heating the detecting element 4. According to the configuration, it is not required to always energize the microheater 2, and, during a period when the microheater 2 is turned OFF and it is determined that the detecting element 4 does not absorb hydrogen, the energization of the microheater 2 can be kept halted. Therefore, the energy required for detecting the hydrogen concentration can be reduced.

When, after the heating operation is started, it is determined that the detecting element 4 stops absorption of hydrogen before the detecting element 4 reaches 60° C. or the reference temperature, it is possible to determine that the hydrogen concentration of the atmosphere is lower than 1%. At this time, therefore, the microheater 2 is turned OFF. As a result, it is possible to prevent the microheater 2 from wastefully consuming energy.

When the operation of the microheater 2 is controlled in this way, it is possible to detect whether the hydrogen concentration of the atmosphere is equal to or higher than 1% or not, and the energization time of the microheater 2 can be greatly shortened. Consequently, the energy required for detecting the hydrogen concentration can be reduced.

Figure 4:
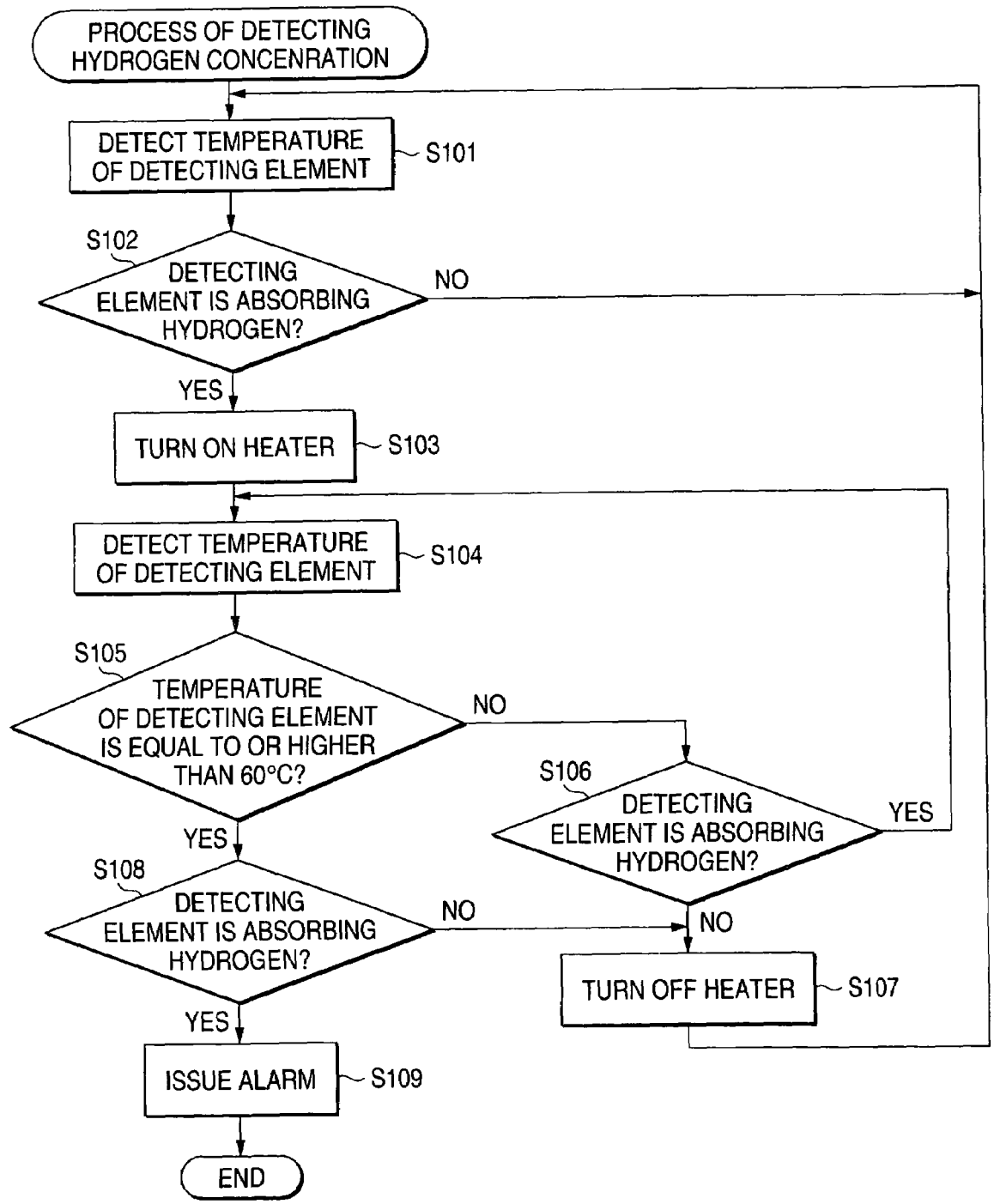
FIG. 4 is a flowchart showing an example of the process of detecting the hydrogen concentration in the hydrogen concentration detecting method of the invention.

Next, a process of detecting the hydrogen concentration in the embodiment will be described with reference to the flowchart of FIG. 4. The control routine of detecting the hydrogen concentration shown in the flowchart of FIG. 4 is implemented at constant time intervals by the controller 10.

First, the temperature of the detecting element 4 is detected in step S101 by the temperature sensor 5.

Next, the process proceeds to step S102 to determine whether the detecting element 4 is absorbing hydrogen or not. The determination of whether the detecting element 4 is absorbing hydrogen or not is conducted based on whether the strain gauge 6 detects strain of the detecting element 4 or not. When the strain gauge 6 detects strain of the detecting element 4, it is determined that the detecting element is absorbing hydrogen, and, when the strain gauge 6 does not detect strain of the detecting element 4, it is determined that the detecting element is not absorbing hydrogen.

If the result of the determination in step S102 is "NO", it is determined that the detecting element 4 is not absorbing hydrogen and hence the hydrogen concentration of the atmosphere is lower than 1%. Therefore, the process returns to step S101.

If the result of the determination in step S102 is "YES" (absorbing hydrogen), the process proceeds to step S103 to enable the heating operation. The microheater 2 is turned ON, and the operation of heating the detecting element 4 is started.

Next, the process proceeds to step S104 so that the temperature sensor 5 detects the temperature of the detecting element 4, and then to step S105 to determine whether the temperature of the detecting element 4 detected in step S104 is equal to or higher than the reference temperature (60° C.) or not.

If the result of the determination in step S105 is "NO" (lower than 60° C.), the process proceeds to step S106 to determine whether the detecting element 4 is absorbing hydrogen or not.

If the result of the determination in step S106 is "YES" (absorbing hydrogen), it is impossible at this stage to determine whether the hydrogen concentration of the atmosphere is equal to or higher than 1% or not. Therefore, the process returns to step S104 so that the ON state of the microheater 2 is continued and the operation of heating the detecting element 4 is continued.

If the result of the determination in step S106 is "NO" (not absorbing hydrogen), it is possible to determine that the hydrogen concentration of the atmosphere is lower than 1%. Therefore, the process proceeds to step S107 to stop (turn OFF) the operation of the microheater 2, and then returns to step By contrast, if the result of the determination in step S105 is "YES" (not lower than 60° C.), it is determined in step S108 whether the detecting element 4 is absorbing hydrogen or not. If the result of the determination in step S108 is "NO" (not absorbing hydrogen), it is possible to determine that the hydrogen concentration of the atmosphere is lower than 1%. Therefore, the process proceeds to step S107 to stop (turn OFF) the operation of the microheater 2, and then returns to step S101.

If the result of the determination in step S108 is "YES" (absorbing hydrogen), it is possible to determine that the hydrogen concentration of the atmosphere is equal to or higher than 1%. Therefore, the process proceeds to step S109 to issue an alarm, and the execution of the routine is ended.

In the embodiment, when the controller 10 implements the process of step S102, the hydrogen absorption determining means is realized. When the controller 10 implements the process of step S103, the heating conducting means is realized, and, when the controller 10 implements the process of step S107, the heating stopping means is realized.

A hydrogen absorbing alloy which absorbs hydrogen discharges the absorbed hydrogen when the hydrogen partial pressure of the atmosphere is lower than the hydrogen equilibrium pressure of the hydrogen absorbing alloy, so that the volume of the alloy returns to the original volume attained before absorption. When the hydrogen partial pressure of the atmosphere is lower than the hydrogen equilibrium pressure of the hydrogen absorbing alloy of the detecting element 4, therefore, the strain gauge 6 does not detect strain.

According to the hydrogen detecting apparatus and the hydrogen concentration detecting method of the embodiment, it is possible to surely detect whether the hydrogen concentration of the atmosphere where the hydrogen detecting apparatus 1 is disposed is equal to or higher than 1% or not. Moreover, the microheater 2 is not always energized. Therefore, the energization time of the microheater 2 can be greatly shortened, and the power consumption of the hydrogen detecting apparatus 1 can be remarkably reduced, with the result that the apparatus is very economical. In the case where the hydrogen detecting apparatus 1 is disposed in a mobile unit, such as a fuel cell vehicle, and operated by a power supply from a battery, particularly, the apparatus is very advantageous because the microheater 2 consumes little power, and the size of the battery to be mounted on the vehicle can be reduced.

In the hydrogen detecting apparatus 1, since the detecting element 4 is made of a hydrogen absorbing alloy, the selectivity with respect to hydrogen is very high, and the hydrogen concentration can be accurately detected. This is very advantageous as compared with a contact combustion type hydrogen detecting apparatus in which hydrogen is detected on the basis of a change in electrical resistance of a detecting element due to catalytic combustion of hydrogen to be detected. In a contact combustion type hydrogen detecting apparatus, a combustible gas other than hydrogen may cause a catalytic reaction, and hence the hydrogen selectivity is poor.

The invention is not limited to the embodiment described above.

In the embodiment, the physical property value which is changed when the hydrogen absorbing alloy absorbs hydrogen is the volume, and a strain gauge is used as means for detecting a volume change. The means for detecting a volume change is not restricted to a strain gauge; however, it may be also configured by other suitable devices.

The physical property value being changed when the hydrogen absorbing alloy absorbs hydrogen may be alternatively the temperature or the weight instead of the volume. In such cases, means for detecting a change of the physical property value may be configured by temperature detecting means or weight detecting means using suitable devices.

In the embodiment, the reference temperature is set to 60° C. The reference temperature is not limited to 60° C., and may be set to an appropriate temperature in accordance with, for example, the atmosphere where the hydrogen detecting apparatus is disposed. In the embodiment, the reference concentration of hydrogen is set to 1%. The reference concentration may be set to an appropriate value in accordance with the intended purpose of the apparatus, and the like.

The structure of the sensor unit shown in FIGS. 1 and 2 configured by the microheater 2, the substrate 3, the detecting element 4, the temperature sensor 5, and the strain gauge 6 is not restricted to that of the embodiment, and may be variously modified. The heating means may be configured by means other than the microheater 2.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

What is claimed is:

1. A hydrogen concentration detecting method of detecting a condition of a hydrogen concentration being equal to or higher than a reference concentration thereof, using a hydrogen detecting apparatus including a detecting element made of a hydrogen absorbing alloy which absorbs hydrogen of a reference concentration at a reference temperature that is higher than an atmospheric temperature; heating means for heating said detecting element; and change detecting means for detecting a change of a physical property value when said detecting element absorbs hydrogen, wherein, when said change detecting means detects a change of the physical property value of said detecting element, said heating means is operated to heat said detecting element, while when said change detecting means does not detect a change of the physical property value of said detecting element, an operation of said heating means is halted.

2. A hydrogen concentration detecting method according to claim 1, wherein, after said heating means is operated, if said detecting element stops absorption of hydrogen prior to a temperature of said detecting element reaching the reference temperature, the operation of said heating means is halted.

3. An apparatus for detecting hydrogen comprising:

a detecting element made of a hydrogen absorbing alloy which absorbs hydrogen of a reference concentration at a reference temperature that is higher than an atmospheric temperature;

heating means for heating said detecting element;

change detecting means for detecting a change of a physical property value when said detecting element absorbs hydrogen;

hydrogen absorption determining means for determining whether said change detecting means detects a change of the physical property value during a state of an operation of said heating means being halted; and heating control means for controlling said heating means to operate when said hydrogen absorption determining means determines that a change of the physical property value is detected.

4. An apparatus for detecting hydrogen according to claim 3, wherein said apparatus further comprises:

temperature detecting means for detecting a temperature of said detecting element; and heating halting means for halting the operation of said heating means when said detecting element stops absorption of hydrogen before a temperature of said detecting element reaches the reference temperature while said heating means is operating.

* * * * *